(12) United States Patent
Singh et al.

(10) Patent No.: US 7,745,631 B2
(45) Date of Patent: Jun. 29, 2010

(54) PROCESS FOR PRODUCING 2-(PHENYL METHYL THIO)-3-PYRIDINE CARBOXYLIC ACID

(75) Inventors: Shailendra Kumar Singh, Uttar Pradesh (IN); Ashutosh Agarwal, Uttar Pradesh (IN)

(73) Assignee: Jubilant Organosys Limited, Uttar Pradesh (IN)

( * ) Notice: Subject to any disclaimer, the term of this patent is extended or adjusted under 35 U.S.C. 154(b) by 912 days.

(21) Appl. No.: 11/547,407

(22) PCT Filed: Jun. 17, 2004

(86) PCT No.: PCT/IN2004/000173

§ 371 (c)(1),
(2), (4) Date: Sep. 29, 2006

(87) PCT Pub. No.: WO2005/097748

PCT Pub. Date: Oct. 20, 2005

(65) Prior Publication Data

US 2008/0139817 A1   Jun. 12, 2008

(30) Foreign Application Priority Data

Apr. 12, 2004   (IN) .................................... 702/04

(51) Int. Cl.
*C07D 213/02* (2006.01)

(52) U.S. Cl. ...................................... 546/298; 546/327

(58) Field of Classification Search ....................... None
See application file for complete search history.

(56) References Cited

U.S. PATENT DOCUMENTS 4,767,766 A * 8/1988 Baker et al. ................. 514/301

FOREIGN PATENT DOCUMENTS

EP          547035 A1 *   3/1987
EP          547305 A1     3/1987

OTHER PUBLICATIONS

International Search Report of International Application No. PCT/IN2004/000173, 2004.
Written Opinion of International Application No. PCT/IN2004/000173, 2004.

* cited by examiner

*Primary Examiner*—Zinna N Davis
(74) *Attorney, Agent, or Firm*—Knobbe Martens Olson & Bear LLP

(57) ABSTRACT

The invention discloses an improved process for producing an intermediate to produce large quantity of 2-(Phenyl methyl thio)-3-pyridine carboxylic acid. The process comprises reacting 2-chloro-3-cyanopyridine with benzyl mercaptan in presence of a base and an aprotic solvent. The resulting intermediate 2-(phenyl methyl thio)-3-cyanopyridine is hydrolyzed in presence of a base in an autoclave and isolated under acidic condition to get the desired product.

20 Claims, No Drawings

PROCESS FOR PRODUCING 2-(PHENYL METHYL THIO)-3-PYRIDINE CARBOXYLIC ACID

RELATED APPLICATIONS

This application is a U.S. National Phase of International Application No. PCT/IN2004/000173, filed Jun. 17, 2004, which claims priority to Indian Application No. 702/DEL/2004, filed Apr. 12, 2004.

FIELD OF THE INVENTION

This invention relates to a process for producing 2-(Phenyl methyl thio)-3-pyridine carboxylic acid, the process consisting of first producing an intermediate to produce large quantity of 2-(Phenyl methyl thio)-3-pyridine carboxylic acid.

BACKGROUND OF THE INVENTION 2-(Phenyl methyl thio)-3-pyridine carboxylic acid is a derivative of pyridine carboxylic acid having a wide range of commercial uses. Pyridine derivatives have, for many years, been investigated for use in the biological sciences like used as an intermediate for the preparation of various agrochemical preparations and in particular, as herbicides, which may be selective to corn.

Processes for producing 2-(Phenyl methyl thio)-3-pyridine carboxylic acid are known. The processes for producing 2-(phenyl methyl thio)-3-pyridine carboxylic acid disclosed in the prior art differ from each other with respect to the different chemical processes employed, use of the different basic raw materials, solvents and further differ in terms of the experimental parameters.

European Patent Numbered EP 0,547,035 to Hanagan Mary ann, discloses a process for preparing 2-(phenyl methyl thio)-3-pyridine carboxylic acid. The disclosed process comprises of making solution of 2-mercapto nicotinic acid, water sodium hydroxide and benzyl chloride, refluxing the solution, diluting with water, acidifying it by adding 36% HCl to get title compound.

Another U.S. Pat. No. 4,767,766 to Baker, et al., discloses the process for the preparation of 2-(phenyl methyl thio)-3-pyridine carboxylic acid comprising making solution of 2-mercapto nicotinic acid, methanol, sodium methoxide and benzyl bromide, stirring the solution, diluting with water, and acidifying the solution till pH 7 with glacial acetic acid to get desired product.

Although the yield of the product by the process mentioned in the prior art are satisfactory, the process is not economically viable because the major raw material 2-mercapto nicotinic acid itself is a high value intermediate.

2-(Phenyl methyl thio)-3-pyridine carboxylic acid is also prepared by reacting 2-chloro nicotinic acid with benzyl mercaptan in presence of a base and an aprotic solvent. Here again, the yield of the desired product is unsatisfactory and hence the process is not economically viable.

The known process suffers from a variety of disadvantages including the fact that during the course of the synthesis of 2-(Phenyl methyl thio)-3-pyridine carboxylic acid, certain impurities like benzyl alcohol is present when benzyl halide is used which is very difficult to isolate from the final product which add to more unwanted step for purification of intermediates and make the process more costly and time consuming. This is extremely disadvantageous in large scale productions of the title compound Therefore, there is a need for an improved process for producing 2-(Phenyl methyl thio)-3-pyridine carboxylic acid especially suitable for large scale manufacture. Large scale manufacturing requires the production of the compound in a cost effective manner.

The invention disclosed herein demonstrates economically viable selective synthesis of intermediate 2-(Phenyl methyl thio)-3-cyano pyridine to manufacture the 2-(Phenyl methyl thio)-3-pyridine carboxylic acid using selective raw materials and appropriate experimental parameters, allowing the process to become industrial friendly for commercial scale and also better yield with high purity.

SUMMARY OF THE INVENTION

It is a principal aspect of the present invention to provide an improved process for producing 2-(Phenyl methyl thio)-3-pyridine carboxylic acid, which is economically viable and is a large scale manufacturing process and obviates the disadvantages mentioned in prior arts.

In one preferred embodiment, disclosed herein is a process for producing 2-(Phenyl methyl thio)-3-pyridine carboxylic acid, by reacting 2-chloro-3-cyanopyridine with benzyl mercaptan in presence of a base and an aprotic solvent.

In one another preferred embodiment, disclosed herein is a process for producing 2-(Phenyl methyl thio)-3-pyridine carboxylic acid, by heating 2-chloro-3-cynopyridine with benzyl mercaptan in presence of a base such as potassium or sodium carbonate in an aprotic solvent such as Dimethyl formamide and then hydrolyzing the resulting intermediate 2-(Phenyl methyl thio)-3-cyano pyridine in presence of a base in autoclave, isolating the resultant in acidic condition to get desired product with high purity and yield.

In yet another preferred embodiment, disclosed herein is a process for producing an intermediate 2-(Phenyl methyl thio)-3-cyano pyridine to produce 2-(Phenyl methyl thio)-3-pyridine carboxylic acid by reacting 2-chloro-3-cyanopyridine with benzyl mercaptan in the presence of a base and an aprotic solvent, wherein the reaction is carried out at a temperature range of 70 to 150° C. and preferably at a temperature between 80 to 140° C.

In yet another preferred embodiment, disclosed herein is a process for producing an intermediate 2-(Phenyl methyl thio)-3-cyano pyridine to produce 2-(Phenyl methyl thio)-3-pyridine carboxylic acid by reacting 2-chloro-3-cyanopyridine with benzyl mercaptan in the presence of a base and an aprotic solvent, wherein the reaction time for producing the intermediate is 2 to 8 hours and preferably 2 to 5 hours.

In yet another preferred embodiment, disclosed herein is a process for producing an intermediate 2-(Phenyl methyl thio)-3-cyano pyridine to produce 2-(Phenyl methyl thio)-3-pyridine carboxylic acid by reacting 2-chloro-3-cyanopyridine with benzyl mercaptan in the presence of a base and an aprotic solvent, wherein the molar ratio of 2-chloro-3-cyanopyridine to benzyl mercaptan is in the range of 1:0.5-3 and preferably 1:0.9-1.2.

In still another preferred embodiment, disclosed herein is a process for producing 2-(Phenyl methyl thio)-3-pyridine carboxylic acid, wherein the reaction temperature for the preparation of 2-(Phenyl methyl thio)-3-pyridine carboxylic acid from intermediate 2-(Phenyl methyl thio)-3-cyano pyridine is 100 to 180° C. and preferably 130 to 160° C.

In still another preferred embodiment, disclosed herein is a process for producing 2-(Phenyl methyl thio)-3-pyridine carboxylic acid, wherein the reaction time for the preparation of 2-(Phenyl methyl thio)-3-pyridine carboxylic acid from intermediate 2-(Phenyl methyl thio)-3-cyano pyridine is 4 to 12 hours and preferably 6 to 9 hours.

In still another preferred embodiment, disclosed herein is a process for producing 2-(Phenyl methyl thio)-3-pyridine carboxylic acid, wherein the reaction pressure for the preparation of 2-(Phenyl methyl thio)-3-pyridine carboxylic acid from intermediate 2-(Phenyl methyl thio)-3-cyano pyridine is 30 to 100 psig and preferably 55 to 75 psig.

In still another preferred embodiment, disclosed herein is a process for producing 2-(Phenyl methyl thio)-3-pyridine carboxylic acid; wherein the process comprises hydrolyzing the intermediate 2-(Phenyl methyl thio)-3-cyano pyridine in presence of a base in autoclave and precipitating the product providing acidic condition by adding hydrochloric acid till pH 3.0.

DETAILED DESCRIPTION OF THE INVENTION

The disclosed embodiment of the present invention deals with a process for the preparation of 2-(Phenyl methyl thio)-3-pyridine carboxylic acid that has advantages over prior art processes in that it avoids formation of undesired product, and eliminates undesired processing steps to make it comparatively time and cost effective process, with high purity and yield.

An improved process for producing 2-(phenyl methyl thio)-3-pyridine carboxylic acid is provided. The process comprises heating 2-chloro-3-cynopyridine with benzyl mercaptan in presence of a base such as potassium or sodium carbonate in an aprotic solvent such as dimethyl formamide and then hydrolyzing the resulting intermediate 2-(Phenyl methyl thio)-3-cyano pyridine in presence of a base in autoclave, isolating the resultant in acidic condition to get desired product with high purity and yield.

Preferred embodiments of the present invention provide a process for producing an intermediate 2-(Phenyl methyl thio)-3-cyano pyridine to produce 2-(Phenyl methyl thio)-3-pyridine carboxylic acid by reacting 2-chloro-3-cyanopyridine with benzyl mercaptan in the presence of a base and an aprotic solvent.

The Amount of benzyl mercaptan and base preferably sodium carbonate or potassium carbonate used in the present invention is in the range of 1 to 3 mole preferably 1 to 1.5 mole per mole of 2-chloro-3-cyanopyridine. If the amount of benzyl mercaptan and base used is less than 1 mole, then the amount of unreacted 2-chloro-3-cyanopyridine will become large, whereas it is economically disadvantageous to use an amount greater than 3 moles. Since then, the effects commensurate with the amount used will not be obtained.

Reaction temperature used in the present invention for producing an intermediate 2-(Phenyl methyl thio)-3-cyano pyridine is in the range of 70-150° C., preferably 80-140° C. If the reaction temperature is less, then the rate of reaction will be low and hence a long time will be required for the reaction. If, on the other hand, the reaction temperature is greater than 150° C., then the rate of reaction will be high, and the product selectivity will be low.

The aprotic solvent used in the process for preparing 2-(Phenyl methyl thio)-3-cyano pyridine, an intermediate to produce large quantity of 2-(Phenyl methyl thio)-3-pyridine carboxylic acid, is selected from a group comprising Perfluorohexane, trifluorotoluene, pentane, hexane, cyclohexane, methylcyclohexane, carbon tetrachloride, toluene, triethyl amine, carbon disulfide, diisopropyl ether, diethyl ether, t-butyl methyl ether, chloroform, ethyl acetate, 1,2-dimethoxyethane, 2-methoxyethyl ether, tetrahydrofuran, methylene chloride, pyridine, 2-butanone, acetone, hexamethylphosphoramide, N-methylpyrrolidinone, nitromethane, dimethylformamide, dimethyl sulfoxide, propylene carbonate or any other aprotic solvent can be used in the process. Dimethyl formamide (DMF) is the most preferred solvent, as it gives surprisingly high yield of the desired product with minimum by product formation.

The present invention provides the process for producing an intermediate wherein the solvent is recovered by distilling under reduced pressure and can be recycled in subsequent batches, and the residue left at bottom is 2-(phenyl methyl thio)-3-cyano pyridine which can be used without any purification in the next step to get a pure and high yield of the title compound.

Obtained residue is hydrolysed in presence of a base in an autoclave followed by isolation under acidic conditions to give the desired product.

Used base in the process can be hydroxide of any alkali metal, preferably sodium hydroxide. The amount used of the base is generally in the range of 1 mole to 4 moles, preferably 1.5 moles to 2.5 moles per mole of 2-(phenyl methyl thio)-3-cyanopyridine.

Preferred embodiments are further illustrated in the following examples:

Example 1

Preparation of 2-(phenyl methyl thio)-3-cyanopyridine 85 g of 2-chloro-3-cyanopyridine, 98.2 g potassium carbonate anhydrous powder and 600 g of dimethyl formamide were mixed to obtain a suspension. To this suspension, a solution of 79.2 g benzyl mercaptan in 250 ml dimethyl formamide was added dropwise over a period of approx. 3 hours at 80-90° C. The reaction mass was agitated for 2 hours at the same temperature. The temperature was slowly raised to 120° C. Then, the reaction mixture was reacted at 120-130° C. for about 1.5 hours. Afterwards, heating was stopped and reaction mass was allowed to attain the room temperature. Inorganic cake was separated by filtration. Dimethyl formamide was distilled under reduced pressure, and the residue left at bottom was 2-(phenyl methyl thio)-3-cyano pyridine 150 g, sufficiently pure to be used in the next step.

Example 2

Preparation of 2-(Phenyl methyl thio)-3-pyridine carboxylic acid 400 g of 12.5% caustic lye solution was taken in an autoclave. To this, 150 g of 2-(phenyl methyl thio)-3-cyanopyridine formed in the previous step was added. The temperature was increased up to 140° C. The reactor pressure was in between 50-75 psig. The reaction mixture was kept for 7 hours at 140-150° C. After hydrolysis, the product was precipitated by adding 35% hydrochloric acid till pH 3.0. Precipitate formed was filtered and washed with water and then dried in an oven to get 135.0 g white to off-white product 2-(Phenyl methyl thio)-3-pyridine carboxylic acid with 90.77% yield (Assay by HPLC 99.49%)

Comparative Example

Example 3

Preparation of 2-(Phenyl methyl thio)-3-pyridine carboxylic acid

In a stirred suspension of 96.37 g potassium carbonate in 700 gm dimethyl formamide, 100 gm 2-chloro nicotinic acid was charged. A solution of 82.38 g benzyl mercaptan in 300 gm dimethyl formamide was added in a period of two hours maintaining reaction temperature 80-90° C. The temperature of the reaction was raised up to 140° C. and then maintained for another three hours. 500 g water was added after completion of the reaction and solvent recovery. Product precipitation achieved by lowering the pH of the reaction mass by using dilute HCl. Product 2-(Phenyl methyl thio)-3-pyridine carboxylic acid precipitated completely till pH 4.5. After filtration and washing, cake was dried to get 110 g white to off white solid product 2-(Phenyl methyl thio)-3-pyridine carboxylic acid with 71.49% yield (Assay by HPLC 99.23%).

Example 4

Preparation of 2-(Phenyl methyl thio)-3-pyridine-carboxylic acid

In a stirred suspension of 96.37 gm potassium carbonate in 700 gm dimethyl sulphoxide, 100 gm 2-chloro nicotinic acid was charged. A solution of 82.38 gm benzyl mercaptan in 300 gm dimethyl sulphoxide was added in a period of two hours maintaining reaction temperature 80-90 deg. c. The temperature of the reaction was raised up to 140 deg. c. and then maintained for another three hours. 500 gm water was added after completion of the reaction and solvent recovery. Product precipitation achieved by lowering the pH of the reaction mass by using dilute HCl. Product 2-(Phenyl methyl thio)-3-pyridine carboxylic acid precipitated completely till pH 4.5. After filtration and washing, cake was dried to get 75.5 gm white to off white solid product 2-(Phenyl methyl thio)-3-pyridine carboxylic acid with 49.07% yield (Assay by HPLC 99.16%).

Certain modifications and improvements of the disclosed invention will occur to those skilled in the art without departing from the scope of invention, which is limited only by the appended claims.

We claim:

1. A process for producing 2-(Phenyl methyl thio)-3-pyridine carboxylic acid, consisting essentially of:
    reacting 2-chloro-3-cyanopyridine with benzyl mercaptan in the presence of a base and an aprotic solvent;
    separating inorganic cake by filtration;
    recovering the aprotic solvent to obtain an intermediate;
    hydrolyzing resulting intermediate in the presence of a base in autoclave;
    isolating the resultant under acidic conditions followed by washing and drying to produce 2-(Phenyl methyl thio)-3-pyridine carboxylic acid.
2. The process according to claim 1, wherein the intermediate is 2-(Phenyl methyl thio)-3-cyanopyridine.
3. The process according to claim 1, wherein the aprotic solvent is dimethyl formamide.
4. The process according to claim 1, wherein the reaction is carried out at a temperature of 70°-150° C.
5. The process according to claim 4, wherein the preferred range of temperature is 80°-140° C.
6. The process according to claim 1, wherein the reaction time for producing the intermediate is 2 to 8 hours.
7. The process according to claim 6, wherein the preferred reaction time is 2 to 5 hours.
8. The process according to claim 1, wherein the molar ratio of 2-chloro-3-cyanopyridine to benzyl mercaptan is in the range of 1:0.5-1:3.
9. The process according to claim 8, wherein the preferred molar ratio is in the range of 1:0.9-1:1.2.
10. The process according to claim 1, wherein the mole ratio of 2-chloro-3-cyanopyridine to base is 1:0.6-1:2.
11. The process according to claim 10, wherein the preferred mole ratio is 1:1-1:1.5.
12. The process according to claim 1, wherein said intermediate produced is usable for hydrolyzing to obtain 2-(Phenyl methyl thio)-3-pyridine carboxylic acid, without purifying the same after the recovery of aprotic solvent.
13. The process according to claim 1, wherein the reaction temperature for producing 2-(Phenyl methyl thio)-3-pyridine carboxylic acid from intermediate is 100° C. to 180° C.
14. The process according to claim 13, wherein the preferred reaction temperature is 130° C. to 160° C.
15. The process according to claim 1, wherein the reaction time for producing 2-(Phenyl methyl thio)-3-pyridine carboxylic acid from intermediate is 4 to 12 hours.
16. The process according to claim 15, wherein the preferred reaction time is 6 to 9 hours.
17. The process according to claim 1, wherein the reaction pressure for producing 2-(Phenyl methyl thio)-3-pyridine carboxylic acid from intermediate is 30 to 100 psig.
18. The process according to claim 17, wherein the preferred reaction pressure is 55 to 75 psig.
19. The process according to claim 1, comprising acidifying the reaction mass obtained after the base hydrolysis, filtering the acidified reaction mass, washing the resultant with water, followed by drying to obtain 2-(Phenyl methyl thio)-3-pyridine carboxylic acid.
20. The process according to claim 1, wherein the process comprising isolating the resultant in acidic condition by adding hydrochloric acid till pH 3.0.

* * * * *